United States Patent
Bunnett et al.

[11] Patent Number: 5,958,407
[45] Date of Patent: Sep. 28, 1999

[54] ILEUS TREATMENT METHOD

[75] Inventors: Nigel W. Bunnett, Sausalito; Carlos U. Corvera, San Francisco, both of Calif.

[73] Assignee: The Regents of the Uinversity of California, San Francisco, Calif.

[21] Appl. No.: 09/049,662

[22] Filed: Mar. 27, 1998

Related U.S. Application Data

[63] Continuation of application No. 08/828,953, Mar. 28, 1997, Pat. No. 5,888,529.
[51] Int. Cl.$^6$ .................................................. A61K 38/48
[52] U.S. Cl. .................. 424/94.64; 424/94.6; 424/94.66; 514/2; 514/12; 514/21
[58] Field of Search .................................. 514/2, 12, 21; 424/94.2, 94.64, 94.66, 94.6

[56] References Cited

U.S. PATENT DOCUMENTS

| | | | |
|---|---|---|---|
| 5,114,917 | 5/1992 | Lezdey et al. | 514/8 |
| 5,217,951 | 6/1993 | Lezdey et al. | 514/8 |
| 5,310,523 | 5/1994 | Smethers et al. | 422/57 |
| 5,362,756 | 11/1994 | Riviere et al. | 514/651 |
| 5,648,355 | 7/1997 | Theoharides | 514/255 |

FOREIGN PATENT DOCUMENTS

553801 B1  8/1994  European Pat. Off. .

OTHER PUBLICATIONS

Clark et al. Tryptase inhibitors block allergen–induced airways and inflammatory responses in allergic sheep. Am J Resp Crit Care Med. vol. 152, 2076–2083, 1995.

Auerswald, E.A., et al., "Recombinant Leech–Derived Tryptase Inhibitor: Construction, Production, Protein Chemical Characterization and Inhibition of HIV–1 Replication," Biol. Chem. 375:695–703 (1994).

Blackhart, B.D., et al., "Ligand Cross–reactivity with the Protease–activated Receptor Family," The Journal Of Biol. Chem. 271(28):16466–16471 (1996).

Böhm, S.K., et al., "Mechanisms of Desensitization and Resensitization of Proteinase–activated Receptor–2," The Journal of Biol. Chem. 271(36):22003–22016 (1996).

Caughey, G. H., "Mast Cell Chymases and Trypases: Phylogeny, Family Relations, and Biogenesis," *Mast Cell Proteases in Immunology and Biology.* New York: Marcel Dekker, Inc. pp. 305–3–29 (1995).

Cochrane, D.E., et al., "Stimulated Rat Mast Cells Generate Histamine Releasing Peptide From Albumin," Peptides 14:117–123 (1993).

Czarnetzki, B.M., et al., "Topical Tiacrilast, a Potent Mast Cell Degranulation Inhibitor, Does Not Improve Adult Atopic Eczema," Dermatology 187:112–114 (1993).

Fitzpatrick, J.C., et al., "Effect of $H_1$ and $H_2$ Receptor Blockers on Mobilization of Myocardial Carnosine to Histamine During Compound 48/80–Induced Shock in Young Rats," Circulatory Shock 30:145–153 (1990).

Gruber, B.L., and L.B. Schwartz, "The Mast Cell as an Effector of Connective Tissue Degradation: A Study of Matrix Susceptibility to Human Mast Cells," Biochemical and Biophysical Res. Comm. 171(3):1272–1278 (1990).

Harvima, I.T., et al., "Mast Cell Tryptase and Chymase in Developing and Mature Psoriatic Lesions," Arch Dematol Res 285:184–192 (1993).

(List continued on next page.)

*Primary Examiner*—Thurman K. Page
*Assistant Examiner*—Lakshmi Channavajjala
*Attorney, Agent, or Firm*—Peter J. Dehlinger; Linda R. Judge; Dehlinger & Associates

[57] ABSTRACT

A method of treating or preventing post-operative ileus in a mammalian subject is disclosed. The method involves administering to the subject, a pharmaceutically effective amount of a compound that is effective in (i) preventing mast cell degranulation, (ii) inhibiting tryptase and chymase, and (iii) antagonizing PAR-2. The treatment is based on the discoveries that proteinase-activated receptor 2 is expressed in colonic muscle cells, and that activation of PAR-2 inhibits colonic motility. The PAR-2 receptor is activated, at least in part, by tryptase and chymase, produced by infiltration and degranulation of mast cells.

3 Claims, 2 Drawing Sheets

OTHER PUBLICATIONS

Hwa, J.J., et al., Evidence for the Presence of Proteinase–Activated Receptor Distinct from Thrombin Receptor in Vascular Endothelial Cells, Circ. Res. 78(4): 581–588 (1996).

Londe, C., et al., "Influence of Platelet Activating Factor Antagonists on the Protamine Sulfate Stimulated Release of Histamine from Peritoneal Mast Cells of Rats in vitro," Arzneim. Forsch/Drug Res. 42(1):27–31 (1992).

Moss, G., et al., "Reducing Postoperative Pain, Narcotics, and Length of Hospitaization," Surgery 206–210 (1986).

Richards, D.M., et al., "Oxatomide A Review of its Pharmacodynamic Properties and Therapeutic Efficacy," Drugs 27:210–231 (1984).

Sekardi and Friedberg, "Inhibition of Immunological Histamine Release from Guinea Pig Lungs and Other Organs by Mepyramine, Ketotifen, and Picumast in vivo," Arzneim,-Forsch./Drug Res. 39(11): 1331–1335 (1989).

Takei,M., et al., "Role of Calcium in Histamine Release from Rat Mast Cells Activated by Various Secretagogoues; Intracellular Calcium Mobilization Correlates with Histamine Release," Biol. Chem. Hoppe–Seyler 370:1–10 (1989).

Vermillion, D.L., and S.M. Collins, "The Non–specific Induction of Mastocytosis in Rat intestinal Muscle," J. Gastrointest. Mot 5:1–8 (1993).

Walter, M., et al., "Inhibition of Human Mast Cell Chymase by Secretory Leukocyte Proteinase Inhibitor: Enhancement of the Interaction by Heparin," Archives of Biochemistry and Biophysics 327(1):81–88 (1996).

ILEUS TREATMENT METHOD

This application is a continuation of U.S. patent application Ser. No. 08/828,953 filed Mar. 28, 1997, U.S. Pat. No. 5,888,529 which is incorporated herein by reference.

FIELD OF THE INVENTION

The present invention relates to a method of treating postoperative ileus.

REFERENCES

Armstrong, R. W., PCT Intl. Appn. Pubn. No. WO 9502566 (January 1995).
Auerswald, E. A., et al., *Biol. Chem. Hoppe Seyler* 375(10):695–703 (1994).
Blackhart, B. D., et al.,*J. Biol. Chem.* 271(28):16466–16471 (1996).
Böhm, S., et al., *J. Biol. Chem.* 271:22003–22016 (1996a).
Böhm, S., et al., *Biochem. J.* 314:1009–1016 (1996b).
Bunin, B. A., et al., *J. Am. Chem. Soc.* 114:10997–10998 (1992).
Bunin, B. A., et al., *Proc. Natl. Acad Sci. USA* 91(11):4708 (1994).
Caughey, G. H., et al., *J. Pharmacol. Exp. Ther.* 264(2):676–682 (1993).
Caughey, G. H., Ed., *MAST CELL PROTEASES IN IMMUNOLOGY AND BIOLOGY*, Marcel Dekker, Inc., New York, N.Y. (1995).
Clark, J. M., et al.,*Am. J. Respir. Crit. Care Med.* 152(6Pt1):2076–2083 (1995).
Galpin, I. J., *Int J Pept Protein Res,* 23(5):477 (1984).
Grinde B., et al, *J Biol Chem* 258(18)10821 (1983).
Gruber, B. L., and Schwartz, L. B., *Biochem. Biophys. Res. Commun.* 171(3): 1272–1278 (1990).
Hannon, J. P., et al., Br J Pharmacol, 115(6):945 (1995).
Harvima, I. T., et al., *Arch. Dermatol. Res.* 285(4):184–192 (1993).
Nystedt, S., et al., *J. Biol. Chem.* 271(25):14910–14915 (1996).
Nystedt, S., et al.,*J. Biol. Chem.* 270(11):5950–5955 (1995).
Pohlig, G., et al., *Eur. J. Biochem.* 241(2):619–626 (1996).
Richards, D. M., et al., *Drugs* 27(3):210–231 (1984).
Scott, R. B., and Tan, D. T., *Can. J. Physiol. Pharmacol.* 74(3):320–330 (1996).
Tabuchi, Y., et al., *Agents Actions* 41(1,2):21 (1994).
Takei, M., et al., *Biol. Chem. Hoppe Seyler* 370(1):1–10 (1989).
Tomkinson, N. P., *Biochem J.,* 286(2):475 (1992).
Vermillion, D. L., and Collins, S. M., *J. Gastrointest. Mot.* 5:1–8 (1993).
Walter, M., et al., *Arch. Biochem. Biophys.* 327(1):81–88 (1996).

BACKGROUND OF THE INVENTION

Inhibition of intestinal motility, especially colonic motility, is a major complication of abdominal surgery. The condition, termed post-operative ileus, delays the normal resumption of food intake after surgery and often leads to prolonged hospitalization.

Mast cells are pro-inflammatory cells that are normally present in the wall of the intestine. Manipulation of intestine and intestinal inflammation are accompanied by influx and degranulation of mast cells in the wall of the intestine (Vermillion). Mast cell tryptase and chymase are proteases that account for 25% of the total protein of mast cells (Caughey, et al., 1993; Caughey, 1995). They are released from mast cells upon degranulation within the wall of the colon.

Heretofore, postoperative ileus has been treated, in extreme cases, with surgical intervention to unblock the colon. Ileus may also be treated with drugs that act to increase colonic motility, such as Leu13-motilin and prostaglandin F2 alpha. However, these approaches have generally been ineffective in significantly reducing the period of postoperative ileus and its complications. It would therefore be useful to provide a more effective method of treating post-operative ileus, in particular, to accelerate recovery time following colonic surgery.

SUMMARY OF THE INVENTION

The present invention is directed to a method of treating or preventing post-operative ileus in a mammalian subject. The method includes administering to the subject, a pharmaceutically effective amount of a compound that is effective in (i) preventing mast cell degranulation, (ii) inhibiting tryptase and chymase, or (iii) antagonizing PAR-2.

The treatment is based on the discoveries that proteinase-activated receptor 2 is expressed in colonic muscle cells, and that activation of PAR-2 inhibits colonic motility. The PAR-2 receptor is activated, at least in part, by tryptase and chymase, produced by infiltration and degranulation of mast cells.

For preventing mast cell degranulation, the compound is preferably cromolyn, doxoantrazole, quercetin, tranilast, ketotifen, tiacrilast, azelastine, lodoxamide, mepyramine, picumast, or water-soluble constituents of the Ginkgo biloba episperm.

For inhibiting tryptase, the compound is preferably leech-derived tryptase inhibitor, APC-366, and BABIM and related amidines, TLCK, GMCHA-Ophbut, or a dipeptide tryptase inhibitor.

For inhibiting chymase, the compound is preferably chymostatin, chymostatin analogues, α-1-antichymotrypsin.

For antagonizing PAR-2, the compound is one capable of inhibiting the mobilization of $Ca^{+2}$ in cells transfected with the PAR-2 gene, and stimulated by trypsin or activating peptide (SLIGKVD-$NH_2$ and SLIGRL-$NH_2$, for human and murine PAR-2, respectively).

Where the treatment compound is a polypeptide, such as leech-derived tryptase inhibitor, chymostatin, chymostatin analogues, and α-1-antichymotrypsin, the compound may be delivered by orally administering a DNA construct capable of transfecting colonic cells, and expressing the polypeptide in the colonic cells.

For orally active compounds, such as cromolyn, doxoantrazole, quercetin, tranilast, ketotifen, tiacrilast, azelastine, lodoxamide, mepyramine, picumast, water-soluble constituents of the Ginkgo biloba episperm, APC-366, BABIM and related amidines, TLCK, and GMCHA-Ophbut, the compound is preferably administered orally. Alternatively, the compound may be administered by parenteral route, such as intraperitoneally or intravenously.

In another aspect, the invention includes a method of identifying compound candidates for use in treating post-operative ileus. The method includes screening test compounds for their ability to inhibit the mobilization of $Ca^{+2}$ in cells transfected with the PAR-2 gene, when the cells are stimulated by trypsin or activating peptide ((SLIGKVD-$NH_2$ or SLIGRL-$NH_2$), and selecting the compound as a candidate for the treatment if significant inhibition of $Ca^{+2}$ mobilization in the cells, when compared with activated cells in the absence of the compound, is observed.

These and other objects and features of the invention will become more fully apparent when the following detailed description of the invention is read in conjunction with the accompanying drawings.

DETAILED DESCRIPTION OF THE INVENTION

The present invention for treating or preventing post-operative ileus is based on the discoveries herein that (i) proteinase-activated receptor 2 is expressed in colonic muscle cells, and (ii) activation of PAR-2 inhibits colonic motility, as detailed in Section I below.

Figure 1:
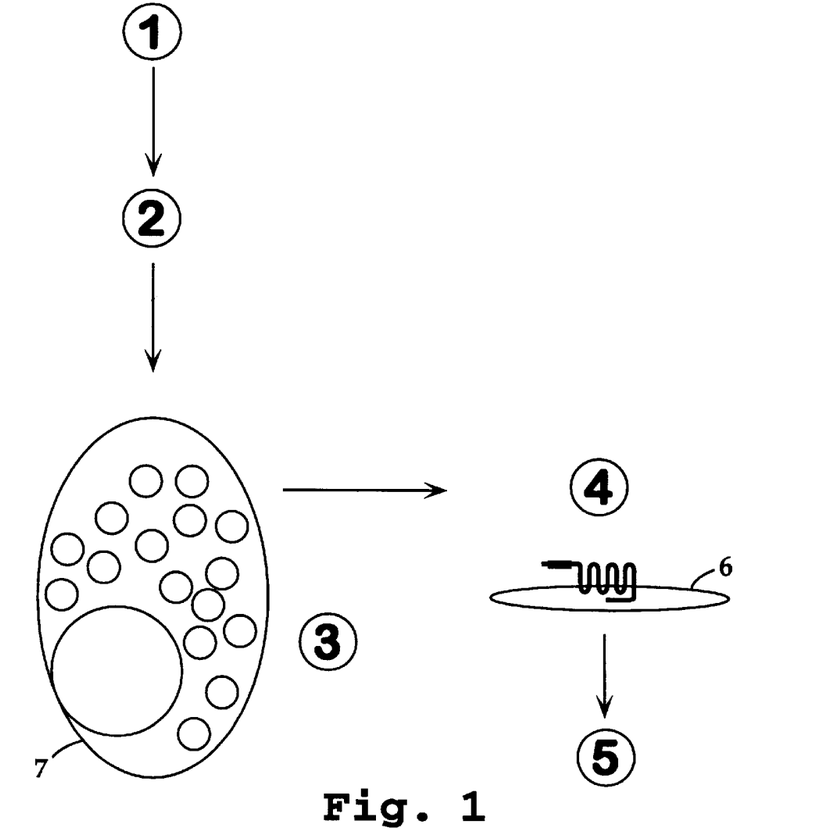
FIG. 1 shows the mechanism of post-surgical ileus, illustrating the points of drug targeting in accordance with the invention.

FIG. 1 shows the mechanism of post-surgical ileus determined from the studies described above. As shown, abdominal surgery (step 1) and intestinal manipulation (step 2) causes infiltration and degranulation of mast cells (7) at colonic sites, with release (step 3) of tryptase and chymase. Both enzymes are capable of specifically cleaving (step 4) PAR-2 on colonic cells (6), releasing the N-terminal SLI-GRL peptide agonist of PAR-2 (step 5) on colonic cells. This activation, in turn, results in loss of colonic cell motility.

The treatment method for post-operative ileus, described in Section II, involves blocking the chain of events between mast-cell infiltration and PAR-2 activation by administering to a compound effective in (i) preventing mast cell degranulation, (ii) inhibiting tryptase and chymase released by mast-cell degranulation, or (iii) antagonizing PAR-2, to prevent its activation by tryptase or chymase.

I. Mechanism of Loss of Colonic Motility

This section describes studies showing that (i) PAR-2 is localized on colonic cells, (ii) is activated by mast-cell proteinases, e.g., tryptase, and (iii) activation of PAR-2 on colonic cells leads to loss of colon cell motility.

1. Localization of PAR-2 in Colonic Myocytes

The proteinase-activated receptor-2 (PAR-2) belongs to family of G-protein coupled receptors, and is activated by specific proteolytic cleavage of its extracellular amino terminus (Nystedt), yielding the amino terminus peptide SLI-GRL or SLIGKVD for murine and human PAR-2, respectively (Blackhart, et al., 1996) which functions as a PAR-2 receptor agonist. Studies conducted in support of the present invention, and discussed in subsections A1–A3 below, show that PAR-2 is highly expressed in smooth muscle in the colon.

a. Localization of PAR-2 in Tissue Sections. Methods for localizing PAR-2 in tissue sections, by indirect immunofluorescence, are given in Example 1. Briefly, PAR-2 was localized in sections of rat colon and in cultured myocytes using antisera to different epitopes, with similar results being obtained with each antiserum. Immunoreactive PAR-2 was prominently localized to the plasma membrane of muscle cells in the circular and longitudinal muscle and the muscularis mucosa. PAR-2 was also detected in colonocytes, especially in the apical regions of cells. Cultured myocytes stained for smooth muscle actin, and thus retain their smooth muscle characteristics. PAR-2 was detected at the plasma membrane and in vesicles of cultured myocytes. Staining of tissues and cells was abolished by preabsorption of the primary antisera with 1–10 $\mu$M of the receptor fragments used for immunization.

Ab. PAR-2 is Expressed by Myocytes. The expression of PAR-2 mRNA in cultured myocytes was examined by RT-PCR, as detailed in Example 2. The study used two rat cell lines (KNRK and hBRIE 380 cells) as positive controls that are known to express PAR-2, and one human cell line (A549) as a negative control that also expresses PAR-2. A PCR product of the predicted 921 kb was amplified using RNA from myocytes, KNRK cells and hBRIE 380 cells, but not from A549 cells. Amplification products from myocytes, KNRK cells and hBRIE 380 cells hybridized with a probe to rat PAR-2, confirming the identity of the amplified fragment as PAR-2.

Ac. $Ca^{2+}$ Mobilization by Colonic Myocytes. The activation of PAR-2 in myocytes was assessed by measuring $Ca^{2+}$ mobilization, as described in Example 3. Trypsin and AP (SLIGRL-$NH_2$) stimulated a prompt increase in $[Ca^{2+}]_i$. Trypsin ($EC_{50}$~1 nM) was 1,000-fold more potent than AP ($EC_{50}$~1 $\mu$M), although trypsin and AP had the same efficacy. There was no $Ca^{2+}$ response to 1 nM trypsin that was pre-incubated with 10 mg/ml SBTI for 60 min at 37° C. before assay, and RP had no effect on $[Ca^{2+}]_i$.

Tryptase stimulated a rapid increase in $[Ca^{2+}]_i$. Tryptase ($EC_{50}$~100 nM) was 100-fold less potent than trypsin ($EC_{50}$~1 nM), but was similarly efficacious. There was no $Ca^{2+}$ response to 40 nM tryptase that was pre-incubated with 1 $\mu$M of BABIM, a selective and potent tryptase inhibitor, or with 1 $\mu$M leupeptin, a serine protease inhibitor, for 5 min at room temperature before assay. Thus, the effect of tryptase depends on its enzymatic activity.

Degranulation of HMC-1 cells (human mast cell line) with substance P was induced, and a filtrate for $Ca^{2+}$ responses in myocytes was assessed, to determine if mast cells release proteases that cleave and activate PAR-2. In preliminary experiments, it was verified that 100 $\mu$M substance P did not stimulate $Ca^{2+}$ mobilization in myocytes (not shown). The HMC-1 mast cell filtrate stimulated a large increase in $[Ca^{2+}]_i$ in myocytes (FIG. 5). The response was inhibited by 46.5±1% by BABIM and 46.5±4% by leupeptin, and is thus dependent to a large extent on tryptase.

2. Mast-Cell Proteinase Activation of PAR-2

In further studies conducted in support of the invention, and detailed in Example 4, it was shown that the responses of myocytes to trypsin, tryptase and AP were mediated by PAR-2. The effect of trypsin on $[Ca^{2+}]_i$ in myocytes was reproduced by a peptide corresponding to the tethered ligand of PAR-2. Mast cell tryptase stimulated $Ca^{2+}$ mobilization in myocytes with a similar efficacy but reduced potency compared to trypsin. The $Ca^{2+}$ response to tryptase in myocytes was abolished by desensitization of PAR-2 with trypsin.

The results indicate that mast cells release tryptase upon degranulation, which regulates myocytes in a paracrine manner by cleaving and activating PAR-2. A filtrate of the degranulated cells stimulated $Ca^{2+}$ mobilization in myocytes, which was inhibited by ~50% by the tryptase inhibitor BABIM, and is thus attributable in large part to tryptase. A filtrate of degranulated mast cells also stimulates $Ca^{2+}$ mobilization in transfected cells expressing PAR-2, but not in non-transfected control cells.

3. Effects of PAR-2 Agonists on Colonic Motility

The results discussed above indicate that colonic muscle expresses PAR-2 and that trypsin, AP and tryptase activate PAR-2 on myocytes. The functional consequences of PAR-2 activation were examined by measuring motility of muscle strips, as detailed in Example 5. Ninety two percent of colon strips (mucosa plus muscle) were spontaneously active. The frequency of contraction was 3.7±0.15/min, the mean amplitude was 1.8±0.2 g, and the maximal amplitude was 2.5 g. Activation of PAR-2 with trypsin and AP caused a concentration-dependent reduction in the mean amplitude of spontaneous contractions. The threshold for inhibition was 300 nM for trypsin and 3 $\mu$M for AP (FIG. 1). Trypsin ($EC_{50}$~500 nM) was 10-fold more potent than AP ($EC_{50}$~5 $\mu$M). The highest concentration of trypsin (3 $\mu$M) inhibited the mean amplitude by 60%, and the highest concentration of AP (30 $\mu$M) inhibited the mean amplitude by 49%, indicating that trypsin is slightly more efficacious than AP. Trypsin (1 $\mu$M) inhibited motility after a delay of 31±5 s, whereas inhibition by AP occurred after a delay of 15±3 s. When tissues were exposed to 1 $\mu$M trypsin or 100 nM AP for 5 min, and then washed extensively, spontaneous activity did not fully recover to basal levels even 6 h after trypsin, whereas activity recovered 5.4±0.34 min after AP. Application of tryptase to the organ bath at concentrations of up to 90 nM did not alter the amplitude of spontaneous contractions. The reason for the lack of inhibition by tryptase is not known, but may be related to its slow rate of diffusion in tissues and difficulties in obtaining sufficiently large amounts of tryptase.

Figure 2:
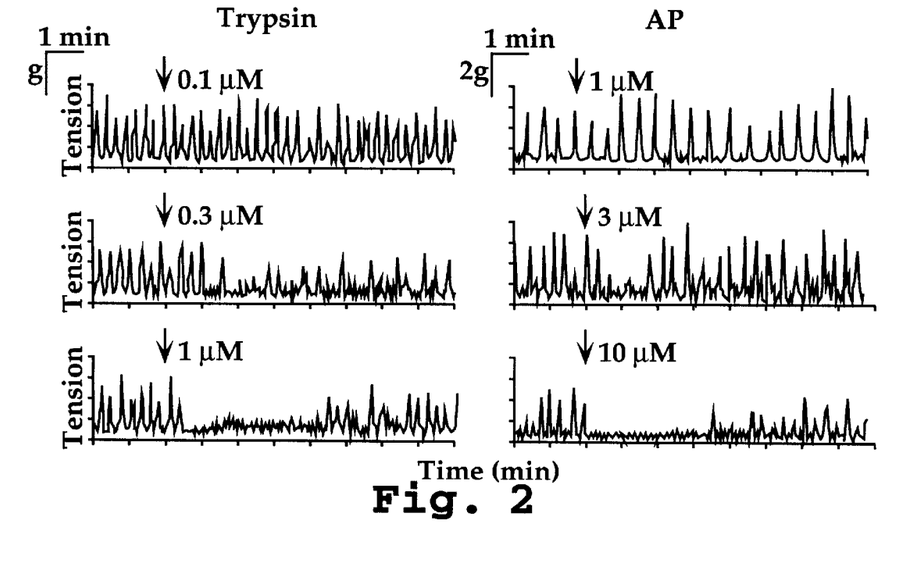
FIG. 2 shows the effect of trypsin (left panels) and AP (right panels) on spontaneous contraction of strips of rat colon, where the traces are from individual strips, but are representative of experiments on strips from at least 4 rats.

Antagonists of various signaling pathways were used to investigate the mechanism by which PAR-2 activation inhibited spontaneous contractions of the colon. Activation of PAR-2 stimulates arachidonic acid release and secretion of $PGE_2$ from enterocytes, and the effects of PAR-2 agonists on gastric muscle are blocked with indomethacin. Although 30 nM $PGE_2$ inhibited colonic motility, pre-incubation of tissues with 1 $\mu$M indomethacin (cyclooxygenase inhibitor) for 15 min had no effect on the response to trypsin and AP. Nitric oxide, which is generated in neurons and muscle cells in the intestine, is an established inhibitor of colonic motility, and the inhibitory effects of PAR-2 agonists on contraction of vascular smooth muscle is mediated by nitric oxide from the endothelium. Although 1 $\mu$M sodium nitroprusside (nitric oxide donor) inhibited colonic motility, pre-incubation of tissues with 100 $\mu$M L-NAME (L-$N^G$-nitro arginine methyl ester, inhibitor of nitric oxide synthase) for 15 min, did not prevent the effects of trypsin and AP (FIG. 2). Trypsin may cleave tissue kininogens to generate kinins, which could inhibit colonic motility. When colonic strips were exposed to 100 nM bradykinin, there was a marked inhibition of spontaneous contractions that was abolished by pre-incubation with 100 nM HOE-140 ($B_2$ receptor antagonist) for 5 min. However, HOE-140 had no effect on the inhibition of colonic motility by trypsin and AP.

Colonic strips were treated with tetrodotoxin (which blocks neuronal $Na^+$ channels) to assess the role of neurotransmission in the inhibitory effects of PAR-2 agonists. Treatment with 1 $\mu$M tetrodotoxin resulted in an immediate and sustained increase in the amplitude and frequency of contractions. However, both trypsin and AP inhibited this elevated motility of tetrodotoxin-treated tissues. The mucosa from colonic strips were stripped to determine if the effects of PAR-2 agonists on motility were due to an indirect action on the mucosa. Removal of the mucosa diminished the spontaneous activity of the colon, so that only 65% of muscle strips were spontaneously active. The frequency of contraction of spontaneously active strips was 1.5±0.2/min, the mean amplitude was 1.2±0.2 g and the maximal amplitude was 2.3 g. However, both trypsin and AP inhibited spontaneous contractions of colonic strips in the absence of the mucosa.

II. Treatment Method

The method of the invention is aimed at blocking the events leading to post-operative ileus, as outlined in FIG. 1. In practicing the method, a compound capable of blocking the pathway from mast-cell infiltration to PAR-2 activation is administered to a subject undergoing abdominal surgery, either pre-operatively or post-operatively.

The dose of compound administered is a pharmaceutically effective amount, as determined, for example, from animal model studies. Dosage levels for many of the compounds useful in the treatment method are known from pharmaceutical references and/or from published articles, such as those cited, and detailed below. The dose can be maintained in a post-operative patient by continue oral administration or IV drip until colonic motility is restored, as evidenced, for example, by easing of abdominal cramping and obstruction.

The compound is preferably administered orally, in the case of an orally active compound. For compounds, e.g., polypeptides, that are susceptible to breakdown in the GI tract, administration may be by intraperitoneal injection, intravenous injection, or other parenteral route, e.g., inhalation.

Alternatively, where the compound to be administered is a polypeptide, administering the compound includes orally administering a DNA construct capable of transfecting colonic cells, and expressing the polypeptide in the transfected cells. Methods for preparing vectors and delivery systems suitable for oral administration are detailed, for example, in PCT application WO96/20732, published Jul. 11, 1996, and in PCT application WO 9640954, published Dec. 19, 1996. Both applications are incorporated herein by reference. Delivery of the DNA construct to cells of the colon can be by way of viral delivery, e.g., an adeno-associated viral vector, or by way of a non-biological carrier, e.g., cationic lipids, such as disclosed in U.S. Pat. No. 5,527,928, which is incorporated herein by reference.

Exemplary polypeptides for delivery via oral gene therapy include chymostatin, chymostatin analogues, and $\alpha$-1-antichymotrypsin, and peptide inhibitors or tryptase. Coding sequences for these polypeptides can be obtained from standard literature and sequence-database resources.

Below are discussed the four classes of compounds useful in the treatment method.

1. Compounds that Inhibit Mast Cell Degranulation

A variety of compounds are known to inhibit mast cell degranulation. Of these, cromolyn (cromolyn sodium or disodium cromoglycate) has been widely studied. Typical doses are 0.5–25 mg/kg per day administered IV, or up to 50 mg/kg/day oral administration (e.g., Hannon).

C48/40 (Tabuchi), may be administered at a dosage range of typically 0.5 to 5 mg/kg IV, subcutaneous, or oral (higher doses for oral administration).

Oxatomide is an orally active compound which inhibits mast cell degranulation (Richards). The drug is administered preferably orally at a dose of between 60–120 mg for adults, e.g., 30 mg after breakfast and 30 mg after dinner. For children, a suitable oral does is about 0.5 mg/kg twice a day.

Other representative compounds effective against mast cell degranulation are the following, along with recommended dosages. Quercitin is an anti-inflammatory agent which is used at an oral does or 1–5 mg/kg at the oral route and up to 5–25 mg/kg. Tranilast can be administered at a doses of 30–100 mg/kg p.o or 3–10 mg/kg IV. A suitable does of ketotifen is 0.25 to 5 mg/kg IV, 0.5 to 5 mg/kg or oral administration, or 5–30 mg/kg i.p. A suitable dose of tiacrilast is 0.5 to 5 mg/kg IV or subcutaneous. Azelastine can be administered at a dose of 1–10 mg/kg oral administration. Lodoxamine at a dosage of 0.01 to 20 mg/kg, preferably 1–5 mg/kg, when administered iv, and oral about 10 mg/kg. Mepyramine at a dose of about 0.2 to 2 mg/kg, preferably about 0.5 mg/kg, is effective. Picumast can be administered at a dose 1–10 mg/kg. Finally, ginkgo biloba extract at a dose of 100–200 mg/kg oral administration. The above dosages represent daily administration levels. Example 8 illustrates the treatment of surgically induced ileus by oral administration of ketotifen.

Also useful are compounds in a class of bis amino, guanidino, and amindino compounds disclosed in PCT patent application WO 95US/11814, which is incorporated herein by reference.

Example
2. Compounds that Inhibit Tryptase

TLCK (tosyl-L-lysine chloromethylketone) is a tryptase inhibitor (Gruber). The compound can be prepared for oral administration at a dose of preferably between 5–50 mg/kg. GMCHA-OPhBut (trans-4-guanidinomethylcyclohexane-carboxylic acid 4-tert butylphenyl ester is known to inhibit tryptase activity, at concentrations of 1–100 $\mu$M. Thus, IV or oral administration of drug at dosage levels effective to achieve this concentration are suitable (Takei).

Another tryptase inhibitor is leech-derived tryptase inhibitor, described, for example, by Auerswald, et al. (1994). The material can be made recombinantly, using reported sequences (Auerswald, et al., 1994; Pohlig). Administration would preferably be by intravenous or intraperitoneal routes, at doses in the range 1–25 mg/kg as needed. Oral administration is a suitable protected formulation designed for release into the colon would also be effective, as would gene therapeutic expression and release as discussed above.

Another tryptase inhibitor, APC-266 (N-(1-hydroxy-2-naphthoyl0-L-arginyl-L-prolinamide HCl (Clark, et al., 1995) can be administered parenterally or orally at a does of preferably between 5–30 mg/kg. BABIM (bis(5-amidino-2-benzimidazolyl) methane) at similar doses is also effective in the treatment method of the invention.

Also useful in the treatment method are dipeptide tryptase inhibitors of the type described in U.S. Pat. No. 5,525,623, and in PCT applications WO 95US/6926 and WO 94US/2706, which are incorporated herein by reference.

3. Compounds that Inhibit Chymase

Two peptide chymase inhibitors are $\alpha$1-antitrypsin and $\alpha$1-antichymotrypsin (Harvima). The peptides can be produced by recombinant methods, and administered parenterally, e.g., by IV or intraperitoneal administration, at dosages in the range 1–20 mg/kg as needed. Oral administration would be suitable by formulating the peptide in a suitable protected formulation designed for release into the colon, as would therapeutic expression and release as discussed above.

Chymostatin, a small peptide inhibitor of chymase, can be administered IV or intraperitoneally at doses in the range 5–25 mg/kg. Also contemplated are a variety of chymostatin analogues, such as described by Galpin, Grinde, and Tomkinson.

Also useful in the treatment method of the invention are pyrimidine and pyridine 1-acetamide chymase inhibitors of the type described in PCT application WO 96JP/1171; 4-sulphinyl triazine derivatives as disclosed in EPO application EP 713876; and imidazoline compounds, as disclosed in PCT application WO 95JP1485, all incorporated herein by reference.

4. Antagonists of PAR-2

In still another aspect, the treatment compound is one capable of inhibiting the mobilization of $Ca^{+2}$ in cells transfected with the PAR-2 gene, and stimulated by trypsin or activating peptide (e.g., SLIGKVD-NH$_2$ or SLIGRL-NH$_2$).

Suitable compounds may be identified by a screening method carried out in accordance with the invention. In this method, cells transfected with the PAR-2 gene, such as the transfected KNRK cells described in Example 6, are activated with a PAR-2 receptor agonist, such as trypsin, chymase, or the activating peptide SLIGRL-NH$_2$ in the presence of the compound(s) being tested for antagonist activity. The PAR-2 activity response can be measured by the cells ability to mobilize $Ca^{2+}$, following the method detailed in Example 7.

A variety of libraries of compounds may be tested in the method, including any of a number of known small-molecule combinatorial libraries, e.g., as described by Armstrong and Bunin. Peptide libraries, e.g., hexamer libraries that are combinatorial in one or more of the residues of the SLIGRL activating peptide are also suitable.

In practice, the transfected cells and test compound(s) are incubated for a period sufficient to allow binding to the PAR-2 receptor. The test compound may be an individual compound or multiple compounds, e.g., the members of a combinatorial library. Agonist, e.g., tryptase or the activating peptide is then added and the cells assayed for their ability to mobilize $Ca^{+2}$, as determined, for example, by the method disclosed in Example 7. Test compounds that show an ability to significantly inhibit $Ca^{+2}$ mobilization in response to PAR-2 activation are considered candidates for use in the treatment method of the invention, and can be further characterized by their ability to bind the PAR-2 receptor, and to stimulate colonic cell motility in animal models of bowel inflammation.

The following examples are intended to illustrate, but in no way limit, the invention.

EXAMPLE 1

Localization of PAR-2 in Tissue Sections

Rats were transcardially perfused with 4% paraformaldehyde in 100 mM phosphate buffered saline, pH 7.4 and 10 $\mu$m frozen sections were prepared. Colonic myocytes were fixed in 4% paraformaldehyde for 20 min at 4° C. PAR-2 was localized by indirect immunofluorescence, as described, using polyclonal antisera raised in rabbits to synthetic fragments of PAR-2 coupled to keyhole limpet hemocyanin. Antiserum B5 (Dr. Morley Hollenberg, University of Calgary) was raised to rat PAR-2: $^{30}$GPNSKGR Ø SLIGRLDT$^{46}$P-YGGC (Ø trypsin cleavage site, YGGC for conjugation). Antiserum PAR-2-C was raised to human PAR-2: Ø $^{37}$SLIGKVDQTSHVTGKG$^{53}$V, and antiserum PAR-2-N was raised to human PAR-2: $^{28}$GTNRSSKGRSL$^{39}$I Ø (Dr. C. Derian, R.W. Johnson Pharmaceutical Research Institute).

EXAMPLE 2

Detection of PAR-2 by RT-PCR and Southern Blotting

Total RNA was reverse transcribed and amplified using the GeneAmp RNA PCR kit (Perkin Elmer, Foster City, Calif., USA). Oligonucleotide primers to rat PAR-2 (sense, 5'-AAGTCTCAGCCTGGCGTGGC-3', +6 to +25; antisense, 5'-ACGACGAGCAGCACGTTGCT-3', +926 to +907) were chosen to bridge the intron of PAR-2, and to amplify a 921 bp fragment. The PCR amplification used 1.5 $\mu$g RNA according to the manufacturer's directions. PCR products were separated on a 1% agarose gel, transferred to a nylon membrane, cross-linked and analyzed by Southern blotting using a probe labeled with digoxigenin-11-dUTP according to the manufacturer's directions (Boehringer Mannheim, Mannheim, Germany). A 162 bp digoxigenin-labeled probe was generated by PCR using a vector containing a rat PAR-2 fragment as a template (from Dr. Morley Hollenberg) and oligonucleotide primers to rat PAR-2 (sense, 5'-TGCTGGGAGGTATCACCCTT-3', +26 to +45; antisense 5'-CATCAACGGAAAAGCCTGGT-3', +187 to +168). The probe was purified using Chroma Spin X-100 columns (Clontech, Palo Alto, Calif.). Membranes were pre-hybridized in 5×SSPE, 10×Denhardt's, 50% deionized formamide, 100 mg/ml salmon sperm DNA and 2% SDS for 3 h at 42° C., and hybridized with probe overnight at 42° C. They were washed 40 min at room temperature in 2×SSC with 0.05% SDS and 20 min at 55° C. in 0.1×SSC with 0.1% SDS. Membranes were incubated with anti-digoxigenin antibody coupled to alkaline phosphatase (Boehringer Mannheim) and developed with BCIP/NBT substrate.

EXAMPLE 3

$Ca^{2+}$ Mobilization

Myocytes were incubated in physiological salt solution (PSS) with 2.5 $\mu$M Fura-2/AM for 20 min at 37° C. Fluorescence was measured in individual cells using an ICCD video camera (Stanford Photonics, Stanford, Calif.) and a video microscopy acquisition program (Axon Industries, Foster City, Calif.). Fluorescence was measured at 340 and 380 nm excitation and 510 nm emission. The ratio of the fluorescence at the two excitation wavelengths, which is proportional to the $[Ca^{2+}]_i$, was calculated. Fresh cells were studied with each agonist and a minimum of 10 cells analyzed in 2–4 experiments on different days.

EXAMPLE 4

Contraction of Muscle Strips

Strips (1 cm long) of rat proximal colon were suspended in an organ bath containing 3 ml of Krebs-Ringer-Bicarbonate gassed with 95% $O_2$/5% $CO_2$ at 37° C. Isometric contractions were recorded and analyzed using Acq-Knowledge 3.1 (BioPac, Santa Barbara, Calif.). A basal tension of 1 g was applied to achieve maximal reproducible spontaneous activity. Tissues were equilibrated for 1 h. The mean amplitude of contraction was determined for 5 min before and after administration of agonists. Data are representative of experiments with at least 4 colon strips from at least 3 different animals.

EXAMPLE 5

Degranulation of Mast Cells

HMC-1 human mast cells (300 $\mu$l of 7×10$^6$/ml in PSS containing 25 $\mu$g/ml heparin) were incubated with 100 $\mu$M substance P for 5 min at room temperature to induce degranulation. The suspension was filtered and assayed for stimulation of $Ca^{2+}$ mobilization. We have previously demonstrated that release of active tryptase is maximal under these conditions.

EXAMPLE 6

PAR-2 Constructs and Cell Lines

Signaling was assessed in KNRK cells stably expressing human PAR-2 (Böhm, 1996a, 1996b). Cleavage was examined in KNRK cells stably expressing human PAR-2 with a POMC signal peptide immediately followed by a Flag epitope (DYKDDDDK) N-terminal to the trypsin cleavage site, and a 12CA5 hemagglutinin epitope (YPYDVPDYA) at the C-terminus (Böhm, 1996b). This construct would be expressed at the cell-surface with an N-terminal Flag sequence, so that loss of surface Flag immunoreactivity could be used to determine rates of cleavage. Studies conducted in support of the invention have shown that the epitope-labeled receptors are appropriately localized to the plasma membrane and signal normally (Böhm, 1996b). KNRK cells were stably transfected with human PAR-2 in pcDNA3 by lipofection. Clonal cell lines were selected and maintained as described (Böhm, 199ba, 1996b). Non-transfected KNRK cells were used for controls.

EXAMPLE 7

$Ca^{2+}$ Mobilization Assay

KNRK cells were plated 24–48 h before experiments on poly-D-lysine coated glass coverslips. They were washed in PSS containing 0.1% BSA, and incubated with 2.5 $\mu$M Fura-2/AM and 0.2% pleuronic for 20 min at 37° C. (Böhm, 1996a). $[Ca^{2+}]_i$ was measured in individual cells in experiments with proteases due to the high sensitivity and small assay volume. Coverslips were mounted in a microincubator in 1 ml PSS at 37° C., and observed using a Zeiss Axiovert 100 microscope with a 40× Fluar objective, a Lambda 10-2 optical filter changer, and a mercury/xenon lamp. Images were captured using an ICCD video camera (Stanford Photonics, Stanford, Calif.) and a video microscopy acquisition program (Axon Industries, Foster City, Calif.). $[Ca^{2+}]_i$ was measured in populations of cells in a spectrofluorimeter (Hitachi Instruments, F-2000) in experiments with tethered ligand peptides. Fluorescence was measured at 340 and 380 nm excitation and 510 nm emission. The ratio of the fluorescence at the two excitation wavelengths, which is proportional to the $[Ca^{2+}]_i$, was calculated.

EXAMPLE 8

Treatment of Ileus by Inhibition of Mast-Cell Degranulation

The aim of this study was to demonstrate that inhibition of mast-cell degranulation is effective in treating surgically induced ileus.

GI transit was measured in fed mice by oral gavage pf 0.3 ml carmine red in methylcellulose. Whole GI transit time was defined as the appearance of the first red fecal pellet. Upper GI transit time was defined as the appearance as the percentage of the distance traveled along the small intestine by the marker in 30 minutes. Cecal manipulation for 5 minutes or skin incision alone was performed under halothane anesthesia and the marker administered 1 hour after surgery.

Figure 3:
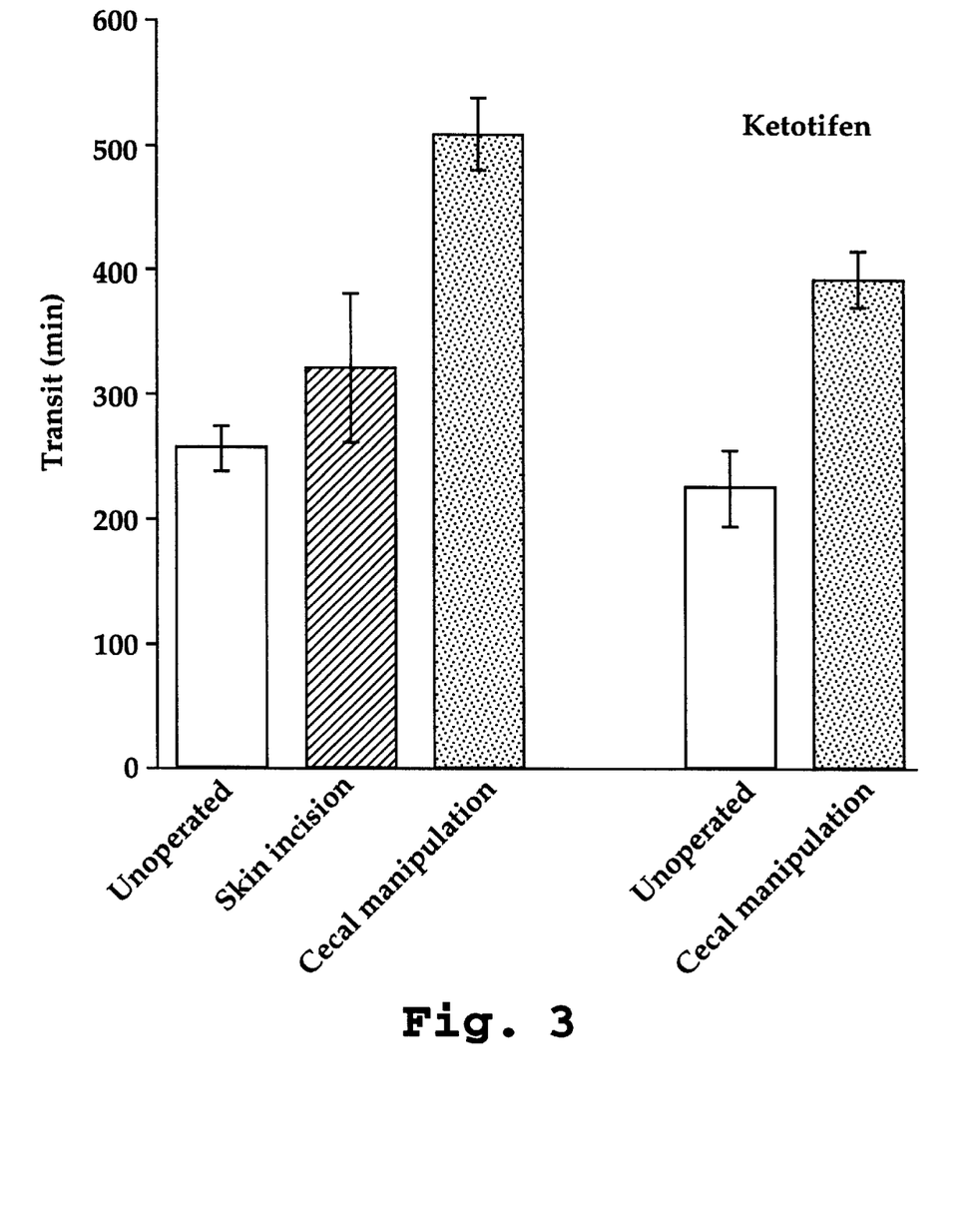
FIG. 3 shows the transit times in mice with cecal manipulation (solid bars) in control and ketotifen-treated animals.

Treatment of surgically induced ileus was by oral administration of ketotifen, at a dose of 1 mg/kg orally 30 minutes prior to anesthesia. The results are shown in FIG. 3. As seen, ketotifen had little effect on the transit time in unoperated animals, but partially reversed inhibition of GI transit produced by abdominal surgery. Skin incision alone had little effect on transit time.

Although the method has been described with respect to specific embodiments and compounds, it will be appreciated that various modification may be made within the scope of the claimed invention.

It is claimed:

1. A method of treating or preventing post-operative ileus in a mammalian subject, comprising administering to the subject, an amount of a compound that is effective in inhibiting tryptase or chymase.

2. The method of claim 1, wherein the compound administered is effective in inhibiting tryptase, and the compound is selected from the group consisting of leech-derived tryptase inhibitor, APC-366, and BABIM and related amidines, TLCK, and GMCHA-OPhBut.

3. The method of claim 1, wherein the compound administered is effective in inhibiting chymase, and the compound is selected from the group consisting of chymostatin, $\alpha$-1-antichymotrypsin, and chymostatin analogs.

* * * * *

UNITED STATES PATENT AND TRADEMARK OFFICE
CERTIFICATE OF CORRECTION

PATENT NO.   : 5,958,407
DATED        : September 28, 1999
INVENTOR(S)  : Bunnett et al.

It is certified that error appears in the above-identified patent and that said Letters Patent is hereby corrected as shown below:

<u>Column 1,</u>
Line 5, insert

-- This invention was made with Government support under contract DK43207 awarded by the National Institute of Health. The Government has certain rights in this invention. --

Signed and Sealed this

Eighteenth Day of February, 2003

JAMES E. ROGAN
*Director of the United States Patent and Trademark Office*